United States Patent [19]

Zadeh

[11] Patent Number: 5,312,455
[45] Date of Patent: May 17, 1994

[54] PROGRAMMABLE WINDOW REFERENCE GENERATOR FOR USE IN AN IMPLANTABLE CARDIAC PACEMAKER

[75] Inventor: Ali E. Zadeh, Sierra Madre, Calif.

[73] Assignee: Siemens Pacesetter, Inc., Sylmar, Calif.

[21] Appl. No.: 67,371

[22] Filed: May 26, 1993

[51] Int. Cl.$^5$ ............................................. A61N 1/365
[52] U.S. Cl. .......................................... 607/26; 607/17
[58] Field of Search .................... 607/17, 18, 25, 26, 607/30; 128/706, 703, 704, 708, 709; 330/69; 322/99, 100

[56] References Cited

U.S. PATENT DOCUMENTS

| | | | |
|---|---|---|---|
| 4,000,461 | 12/1976 | Barber et al. | 128/708 |
| 4,458,692 | 7/1984 | Simson | 128/705 |
| 4,556,062 | 12/1985 | Grassi et al. | 607/26 |
| 4,596,255 | 6/1986 | Snell et al. | 128/697 |
| 4,712,555 | 12/1987 | Thornander et al. | 607/17 |
| 4,817,805 | 4/1989 | Sholder | 607/28 |
| 4,940,052 | 7/1990 | Mann et al. | 607/30 |
| 4,989,602 | 2/1991 | Sholder et al. | 605/4 |
| 5,010,887 | 4/1991 | Thornander | 128/696 |

OTHER PUBLICATIONS

Fredericksen, *Intuitive IC Electronics: A Sophisticated Primer for Engineers and Technicians*, McGraw Hill (1987).

Hodges & Jackson, *Analysis and Design of Digital Integrated Circuits*, McGraw Hill (1983).

Millman & Grabel, *Microelectronics*, McGraw Hill, pp. 728-751 (1987).

*Primary Examiner*—William E. Kamm
*Assistant Examiner*—George Manuel
*Attorney, Agent, or Firm*—Bryant R. Gold; Malcolm J. Romano

[57] ABSTRACT

A sense amplifier adapted for use with a cardiac pacer or the like includes a constant gain filter, a window comparator circuit and a programmable threshold reference generator circuit. The reference generator circuit generates a programmable window (reference) voltage used by the window comparator circuit to determine whether an input signal, amplified by the constant gain filter, exceeds the window voltage. The reference generator circuit is based on a bipolar junction device having an adjustable emitter area through which a constant current flows. The emitter area is adjusted in response to a control signal. As the emitter area changes as controlled by the control signal, the voltage across the device changes. In a preferred embodiment, a parallel combination or network of switched bipolar junction devices is used to realize the adjustable emitter area. The bipolar junction devices are switched into and out of operation in response to the control signal, thereby increasing or decreasing the net emitter area of the network. When the constant current flows through the network, a precisely controlled adjustable reference voltage is thus generated as a function of the net emitter area.

23 Claims, 5 Drawing Sheets

PROGRAMMABLE WINDOW REFERENCE GENERATOR FOR USE IN AN IMPLANTABLE CARDIAC PACEMAKER

BACKGROUND OF THE INVENTION

FIELD OF THE INVENTION

The present invention relates to cardiac event detection, and more particularly, to circuits and methods for accurately generating a programmable reference signal(s) that may be used by threshold detector circuits within a sensing channel of an implantable cardiac pacemaker.

The major pumping chambers in the human heart are the left and right ventricles. The simultaneous physical contraction of the myocardial tissue in these chambers expels blood into the aorta and the pulmonary artery. Blood enters the ventricles from smaller antechambers called the left and right atria which contract about 100 milliseconds (ms) before the ventricles. The physical contractions of the muscle tissue result from the depolarization of such tissue, which depolarization is induced by a wave of spontaneous electrical excitation which begins in the sinus node of the right atrium, spreads to the left atrium and then enters what is known as the AV node which delays its passage to the ventricles via the so-called bundle of His. The frequency of the waves of excitation is normally regulated metabolically by the sinus node. The atrial rate is thus referred to as the sinus rate or sinus rhythm of the heart.

Electrical signals corresponding to the depolarization of the myocardial muscle tissue appear in the patient's electrocardiogram. A brief low amplitude signal, known as the P-wave, accompanies atrial depolarization. A much larger amplitude signal, known as the QRS waveform complex, having a predominant R-wave, signifies ventricular depolarization. Repolarization prior to the next contraction is marked by a broad waveform in the electrocardiogram known as the T-wave.

A typical implanted cardiac pacer (or pacemaker) operates by supplying missing stimulation pulses through an electrode on a pacing lead in contact with the atrial or ventricular muscle tissue. The electrical stimulus independently initiates depolarization of the myocardial (atrial or ventricular) tissue, resulting in the desired contraction. Advantageously, electrical signals corresponding to the P-wave or R-wave can be sensed through the same lead, i.e., the pacing lead, and may thereafter be used as a timing signal to synchronize or inhibit stimulation pulses in relation to spontaneous (natural or intrinsic) cardiac activity. Such sensed signals are referred to as an atrial electrogram signal (corresponding to the P-wave) or a ventricular electrogram signal (corresponding to an R-wave).

Every modern-day implantable pacemaker includes a sensing or threshold circuit, whether the activity of one or both chambers of the heart are sensed. When the electrical signal of the atrial or ventricular electrogram is coupled from the heart into the pacemaker, the electrical signal is typically passed through a series or group of electrical circuits referred to as the sensing channel. One of the primary functions of the sensing channel is to detect the presence of particular waveforms within the electrogram signal, e.g., the QRS waveform complex, and to generate a trigger signal whenever such particular waveforms are present, and to not generate such trigger signal when such waveforms are not present. In this way, the sensing channel thus monitors the heart for the occurrence of particular cardiac events, e.g., atrial and/or ventricular depolarization.

Heretofore, the sensing channel has typically included the following electrical circuits: a programmable gain filter, a gain decoder, a window comparator and a constant reference voltage generator. Such circuits, in combination, are frequently referred to as the "sense amplifier." The programmable gain filter receives the electrogram signal and, in operation, filters and amplifies the electrogram signal by a prescribed amount before presenting a filtered, amplified electrogram signal to the window comparator. The gain of the programmable gain filter is controlled so that the amplitude of the filtered, amplified electrogram signal will be sufficient to trigger the window comparator whenever the particular waveform to be detected is present within the electrogram signal, and will be insufficient to trigger the window comparator whenever the particular waveform is not present within the electrogram signal. A threshold or window voltage, typically generated by the constant reference generator, is used to define when the filtered, amplified electrogram signal amplitude is of sufficient amplitude to trigger the window comparator. The presence or absence of the trigger signal generated by the window comparator is then used to control the other circuits within the cardiac pacer.

The gain decoder, coupled to the programmable gain filter, generates a gain signal that controls the gain of the programmable gain filter. The gain signal is set (generated) in response to a gain code received from the other circuits of the cardiac pacer. In order to produce the specified gain, the programmable gain filter includes a bank of switched capacitors that are programmably switched in and out, or substituted, for each other within the programmable gain filter's amplifier circuit. As these capacitors are switched in and out of the programmable gain filter circuit, the gain of the filter circuit changes, as is known in the art.

The internal circuits of an implantable cardiac pacer are typically integrated into a single integrated circuit or "chip." The use of such integrated circuit chip offers the advantage of providing a circuit that is much smaller than similar circuits constructed either partially or completely from discrete components.

A sense amplifier realized using an integrated circuit chip typically consists of a programmable gain filter. The gain of such filter is programmed by switching capacitors in and out of the circuit. The gain of any switched-capacitor filter depends primarily on the ratio of two capacitors (usually the ratio of an input capacitor to a feedback capacitor). The absolute values of capacitors used in integrated circuit chips may vary as much as ±20% from chip to chip, wafer to wafer, or run to run. Such variations, however, do not necessarily translate to a gain change of ±20%. That is, as explained below, the gain is set by the ratio of capacitors, and a variation of one capacitor, e.g., the input capacitor, is almost always accompanied by a corresponding variation in the other capacitors used on the same chip. Hence, even though the absolute values of capacitors used in integrated circuit chips may vary over a wide range, the ratio of two reasonably sized capacitors, e.g., 1-5 pf, may have a tolerance as low as ±0.2%. Hence, the use of a switched-capacitor filter has heretofore provided the basis for an accurate programmable gain within the sense amplifier of a pacemaker.

To illustrate, it is noted that the value of a rectangular integrated circuit capacitor is $$C = \frac{E_{ox}}{t}(WL)$$

where C is the capacitor value, $E_{ox}$ is the permittivity of silicon dioxide (a constant), t is the oxide thickness between the capacitor plates, W is the width of the capacitor edge, and L is the length of the capacitor edge. In a given integrated circuit chip, the capacitance value can thus vary as a function of variations in the width W, length L, or oxide thickness t. Since these parameters are poorly controlled during integrated circuit fabrication, the absolute value of the capacitor may change as much as ±20% from chip to chip, or wafer to wafer, or run to run.

Fortunately, for a parameter such as gain, the value of the parameter is a function of the ratio of two capacitors, e.g., an input capacitor $C_1$ and a feedback capacitor $C_2$. That is, the gain, G, of the filter may be expressed as $$G = (k)\frac{C_1}{C_2}$$

where k is a constant factor. The variation of gain, ΔG, as a function of variations of capacitors may thus be expressed as $$\frac{\Delta G}{G}G = \frac{\Delta C_1}{C_1} - \frac{\Delta C_2}{C_2}.$$

Thus, in a specific integrated circuit, where both $C_1$ and $C_2$ will almost always increase or decrease by the same amount (because both will normally experience the same variations in width W, length L, and/or oxide thickness t), any parameter such as gain (G) will theoretically not change at all. (The ±0.2% indicated above comes from other second order effects, such as randomness of capacitor edges within the integrated circuit.)

The above discussion and analysis is valid only when the values of the capacitors used in the switched-capacitor filter are reasonably high, e.g., on the order of 1-2 pf. That is, when reasonable value capacitors are used (1-2 pf), the variation of edges are insignificant compared to the size of the total capacitor value. Further, even though there are parasitic (unwanted) capacitors that are always present within an integrated circuit chip (due, e.g., to the conductive traces or layers that interconnect the various circuit elements within the chip), the value of such parasitic capacitors is usually small and therefore negligible (or at least tolerable) compared to the desired capacitance value. Typically, parasitic capacitors are in parallel with the desired capacitors, and they thus tend to increase the overall capacitance value. While it is possible to minimize parasitic capacitance by using intelligent routing of the traces used within the integrated circuit layout, it is impossible to completely eliminate them. Moreover, some parasitic capacitors are hard to predict or model. Thus, heretofore, the only effective way of dealing with parasitic capacitors in switched-capacitor filters, and other integrated circuit chips, has been to design the circuits with capacitor values that are significantly higher than the inherent parasitic capacitance.

Unfortunately, there is a drawback to designing high value capacitors (e.g., capacitors on the order of 1-2 pf or greater) into the programmable filter of a sense amplifier of a cardiac pacemaker when such programmable filter is part of an integrated circuit. When the capacitance value is relatively high, the capacitors (as they are switched into and out of the circuit, and as they perform their desired signal processing functions within the designed circuits) must be charged and discharged by the other pacemaker circuits (usually operational amplifiers). Such charging and discharging translates to a higher current consumption for the operational amplifiers (or other circuits). A high current consumption, of course, is not desirable within an implanted pacemaker, because such current consumption translates to a shorter battery life. Moreover, in order to realize a higher gain, the input capacitor value may have to become very large, which means the capacitor physically occupies a significant amount of space ("real estate") on the integrated circuit chip. In order to design of a programmable gain filter on a chip within an implanted pacemaker that has reduced current consumption, and that occupies an acceptable amount of space, it would be desirable to use capacitors having values on the order of 0.1 to 0.2 pf. Unfortunately, for these values of capacitors, the inherent parasitic capacitance on the chip is significant, and can disadvantageously corrupt the gain value of the programmable gain filter. Thus, there is a need in the art for a programmable gain filter design that allows small capacitance values to be used, thereby reducing current consumption and occupying less chip real estate, while still providing an accurate way to programmably control the gain of the filter.

As an example of the type of gain control that is needed within a sense amplifier (programmable gain filter) of an implantable pacemaker, consider a programmed change in the sensitivity level from 7.75 mV to 8 mV. Such a change may require that the gain of the filter change from 20.65 to 20.0, or about 3%. Such a precise gain change in a switched-capacitor programmable gain filter using small capacitance values (0.1 to 0.5 pf) has heretofore been impossible to realize.

The term "sensitivity" when referring to the sensing channel (or sense amplifier) of a pacemaker reflects the proneness of the sensing channel to generate a trigger signal. A more sensitive sense amplifier generates a trigger signal in response to lower amplitude electrogram signals than will a less sensitive sense amplifier. A related parameter to the sensitivity is the "sensitivity level" of the sense amplifier. The sensitivity level is the unamplified amplitude of the electrogram signal at which the amplified electrogram signal triggers the window comparator. Thus, as the sensitivity level of the sense amplifier decreases (i.e., as the minimum amplitude of electrogram signal needed to generate a trigger signal decreases), the sensitivity of the sense amplifier increases (i.e., the sense amplifier becomes more prone to generate a trigger signal). Unfortunately, because the typical window comparator generates its trigger signal based upon a comparison of the amplified filtered electrogram signal with a constant threshold or window voltage, the sensitivity level cannot be increased or decreased in uniform increments, e.g., of 0.25 mV, unless the steps in the gain of the gain filter are inversely adjusted. That is, if the sensitivity level is to increase (i.e., if the sensitivity is to decrease), the steps in gain, or gain steps, must become smaller; and if the sensitivity level is to decrease, the gain steps must become larger.

Problematically, when small capacitance values are used within a switched-capacitor programmable gain filter, as indicated above, it is not possible to achieve the type of gain precision that may be needed. That is, at high sensitivity levels, the programmable gain filter may not have sufficient precision to assure that the window comparator is triggered or not triggered when appropriate. For example, for an increase in sensitivity level from 0.25 mV to 0.5 mV (a 0.25 mV increase in sensitivity level), and assuming a constant threshold or window voltage of 160 mV above which the amplified filtered electrogram signal must reach before a trigger signal will be generated, the gain must decrease from 640 to 320, a decrease in gain of 320, or 100%. However, for an increase in sensitivity from 7.75 mV to 8.0 mV (also a 0.25 mV increase in the sensitivity level) the gain must decrease from 20.65 to 20.00, a decrease in gain of only 0.65, or roughly 3%. As mentioned above, gain changes on the order of 3% are, at best, difficult to achieve under the best of circumstances, but are essentially impossible to realize when small capacitors (0.1–0.5 pf) are used as part of the integrated circuit design.

Furthermore, as also mentioned above, the gain of the programmable gain filter is typically directly proportional to the capacitance of the capacitors that are substituted into the programmable gain filter circuit. Thus, at low sensitivity levels, and thus high gains, the capacitance needed is quite large relative to the capacitance needed at higher sensitivity levels. Such large capacitances are difficult to fabricate using integrated circuit technology and require large chip areas.

A further disadvantage of the existing programmable gain filter is that, in addition to being imprecise, its gain steps may be polytonic. That is, as the gain code is increased, the gain will generally increase, but because of the poor precision in the switched capacitors, some of the gain steps may be negative, causing an unpredictable decrease in the gain. To further complicate this problem, such "negative gain steps" may not appear uniformly in the fabrication of an integrated circuit chip. Thus, several sense amplifiers fabricated together may exhibit negative gain steps in response to different gain codes. The existence of such polytonic operation thus requires individual circuit testing, advanced programming and/or additional circuitry to correct.

It is therefore evident that improvements are needed in the sense amplifier circuits used within implantable cardiac pacers, and similar implantable medical devises.

SUMMARY OF THE INVENTION

The present invention provides an improved sense amplifier and method of operation for use within cardiac pacers or similar implantable devices. More specifically, the invention provides an improved, low-power, window voltage generator circuit that generates the threshold or window voltage used to determine the "sensitivity" and/or "sensitivity level" of the sense amplifier of a cardiac pacer. Advantageously, the present invention improves upon known window voltage generators in terms of reduced power consumption, accuracy of the generated threshold voltage, and the precision achievable in operation using conventional integrated circuit fabrication processes. As a result, the present invention, in response to a window control signal, always produces a monotonic output window, i.e., a sequence of increasing or decreasing threshold voltages as a function of an increasing or decreasing window control signal.

One embodiment of the invention can be viewed as a threshold voltage generator circuit that uses a bipolar junction device with an adjustable emitter area. The emitter area is adjusted in response to the window control signal. As a result, the voltage across the junction device changes in a controlled manner, which voltage change is used to define the changes in the threshold voltage.

For example, in accordance with the present invention, a parallel combination or network of bipolar junction devices may be switched into and out of operation in response to a gain control signal so as to increase or decrease the net emitter area of the network. By causing a constant current to flow through the network regardless of the net emitter area switched into the network, an accurately controllable reference voltage is developed across the network.

Advantageously, the invention may be used in a sense amplifier of a cardiac pacer along with a constant gain filter, a decoder, and a window comparator to control the sensitivity of the sense amplifier. When thus used, the reference voltage generated by the invention defines a threshold (or window) voltage that, when decreased, increases the sense amplifier's sensitivity, and that, when increased, decreases the sense amplifier's sensitivity, as explained above. Thus, it is a feature of the present invention to provide an improved reference voltage generator for use in sense amplifiers of cardiac pacers.

It is a further feature of the invention to provide an improved programmable reference voltage generator that can be readily fabricated using integrated circuit technology.

It is another feature of the invention to provide such a programmable reference voltage generator wherein precise regulation of the reference voltage is possible.

It is still an additional feature of the invention to generate a precision yet programmable reference voltage that can be increased or decreased monotonically.

It is yet another feature of the present invention to provide a reference voltage generator that can be fabricated such that steps in the generated threshold reference voltage may be linear, logarithmic, or other specified types, in any step size.

BRIEF DESCRIPTION OF THE DRAWINGS

The above and other aspects, features and advantages of the present invention will be more apparent from the following more particular description thereof, presented in conjunction with the following drawings wherein like numbers have been used to refer to substantially identical elements.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
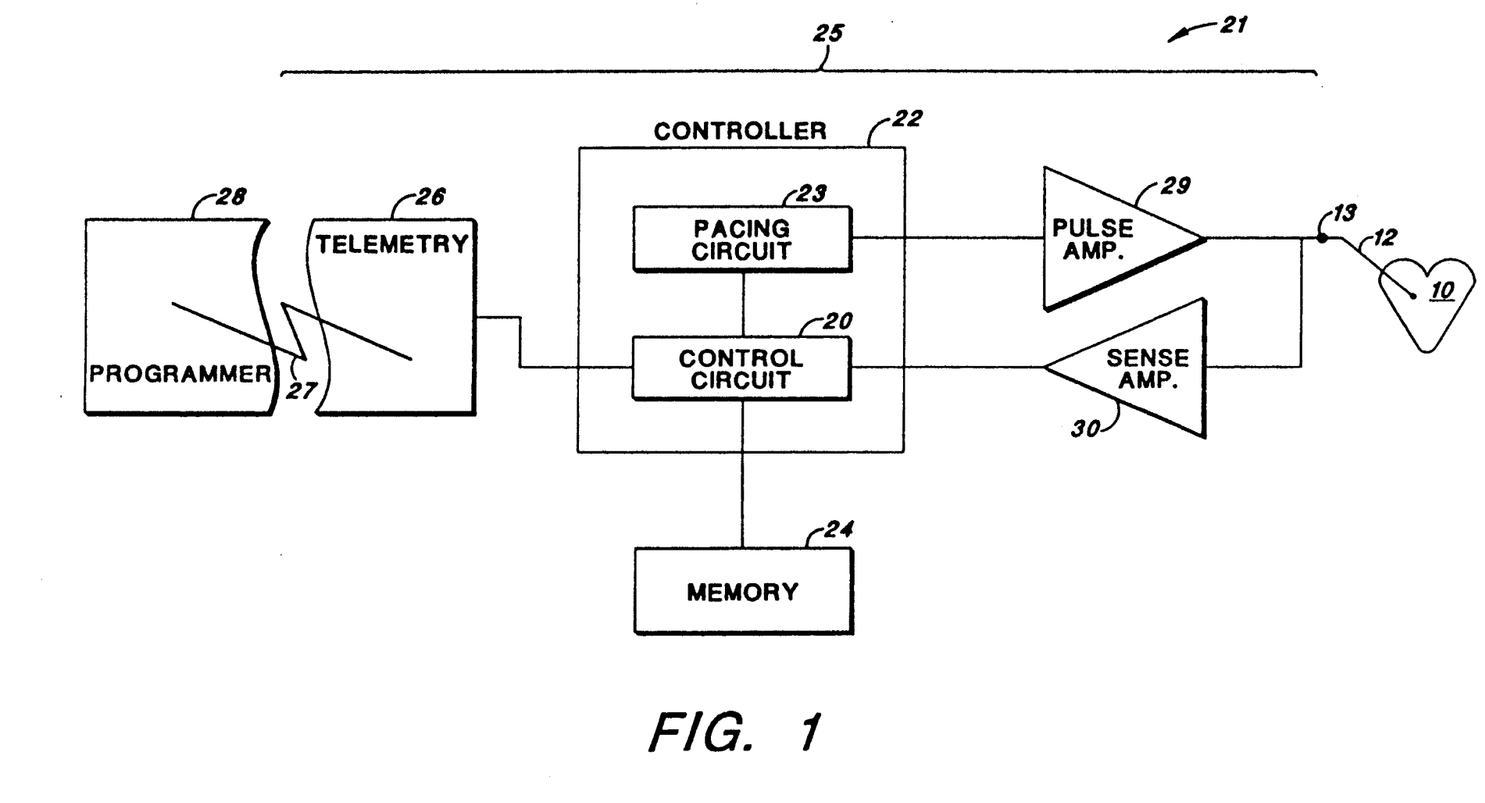
FIG. 1 is a block diagram of a cardiac pacer.

Referring to FIG. 1, a block diagram is shown of a cardiac pacer (or cardiac pacing system) 21. The cardiac pacing system 21 includes an implantable device 25 that, when implanted into a patient, is coupled to a heart 10 of the patient via an electrogram or pacing lead 12. The electrogram lead 12 provides electrical communication between the implantable device 25 and the heart 10. The lead 12 is coupled to the device 25 at a connection point 13. The connection point may be a detachable coupling wherein the electrogram lead 12 may be coupled to and decoupled from the implantable device 25. One signal that is communicated through the electrogram lead 12 from the heart 10 to the implantable device 25 is an electrogram (or input) signal, which electrogram signal evidences cardiac activity (i.e., depolarization of the atria and/or ventricles), or the absence of cardiac activity. The implantable device 25 is housed in an implantable, hermetically sealed housing (not shown) as is known in the art of implantable electronic pacemakers.

The cardiac pacer 21 includes a pacing controller 22, comprised of a pacing circuit 23 and a control circuit 20; a memory circuit 24; a telemetry circuit 26; a pulse amplifier 29; and a sense amplifier 30.

The pulse amplifier 29 and the sense amplifier 30 are coupled to the electrogram or pacing lead 12. Generally, the same lead 12 serves to provide both pacing and sensing functions. Thus, the connection point 13 is generally a single coupling between the lead 12 and the implantable device 25. However, it is contemplated that the lead 12 may be two or more separate leads. As a result, the electrogram lead 12 may, e.g., be coupled to the first connection point and be used for sensing, and another lead, used for pacing, may be coupled to a second connection point. For purposes of illustration, the configuration of FIG. 1 is assumed to include only a single lead 12 and a single connection point 13, which single lead serves both to communicate the electrogram or input signal to the implantable device 25 (the electrogram signal), and to communicate the therapy or the therapeutic output signal to the heart 10 (e.g., a stimulation pulse signal).

The pulse amplifier 29 is also coupled to the pacing circuit 23. The pacing circuit 23 initiates the therapy delivered to the heart by the pulse amplifier 29 via the lead 12. The pacing circuit 23 operates in response to the control circuit 20, which determines the appropriate therapy to deliver to the heart.

In determining what is optimum therapy, the control circuit 20 may use a memory 24. Various control parameters may be stored in the memory 24 by a physician using a telemetry circuit 26, which is also coupled to the control circuit 20. In order to store such control parameters in the memory 24, the physician utilizes an external (non-implanted) programmer 28 that is coupled to the control circuit 20 via the telemetry circuit 26 and a suitable noninvasive communication link 27. The communication link 27 may include, e.g., capacitive or inductive coupling and functions to allow communications between the programmer 28 and the telemetry circuit 26 as is known in the art.

The control circuit 20 is also coupled to the sense amplifier 30. The sense amplifier 30 filters the incoming electrogram signal from the heart 10 so as to eliminate "noise" and other unwanted components of the electrogram signal, e.g., the low frequency T-wave. In addition, the sense amplifier 30 amplifies the electrogram signal. Finally, the sense amplifier 30 detects whether or not the filtered, amplified electrogram signal exceeds a threshold or window voltage, and if the filtered, amplified electrogram signal does exceed the window voltage, the sense amplifier generates a threshold detect or trigger signal.

Figure 7:
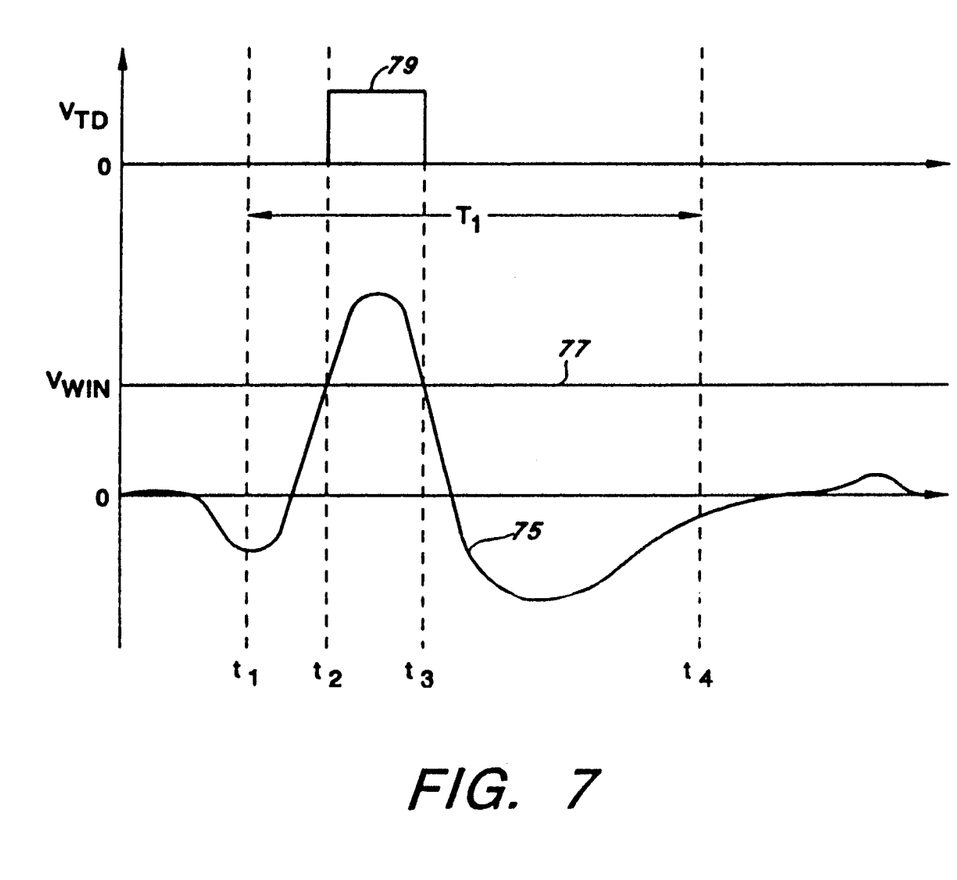
FIG. 7 illustrates an electrogram signal with an amplitude represented on the vertical (or voltage) axis and time represented on the horizontal (or time) axis, and further illustrates how a threshold or window voltage is used to determine when a particular waveform is present in the electrogram signal.

Referring momentarily to FIG. 7, an example electrogram signal 75 is shown (on a vertical or voltage axis and a horizontal or time axis). The electrogram signal 75 includes a QRS waveform complex 76 that exceeds a window voltage ($V_{WIN}$) between the times $t_2$ and $t_3$. In response to the electrogram signal 75 exceeding the window voltage ($V_{WIN}$) 77 the sense amplifier 30 generates the trigger signal ($V_{TD}$) 79 as is shown from time $t_2$ to time $t_3$.

Referring back to FIG. 1, the control circuit 20 receives the trigger signal from the sense amplifier 30 and, in response thereto, evaluates whether or not optimum therapy is being delivered to the heart 10, based on both the trigger signal and the parameters stored in the memory 24. If the therapy being delivered is not optimum, the control circuit 20 makes adjustments, as required, to the pacing circuit 23. In response to the adjustments, the pacing circuit 23 begins delivering a more optimum therapy to the heart 10 via the pulse amplifier 29.

Alternatively, various therapy circuits other than the pacing circuit 23 may be utilized with the cardiac pacer 21 of the present invention, such as stimulators, implantable electrical defibrillators, implantable monitoring devices, and the like.

The pulse amplifier 29, controller 22 (including the pacing circuit 23 and control circuit 20), memory 24, telemetry circuit 26, and programmer 28 may be of conventional design, as is shown, e.g., in U.S. Pat. Nos. 4,596,255; 4,712,555; 4,817,605; and 4,940,052; incorporated herein by reference. The present invention is directed primarily to improvements in the sense amplifier 30.

Figure 2:
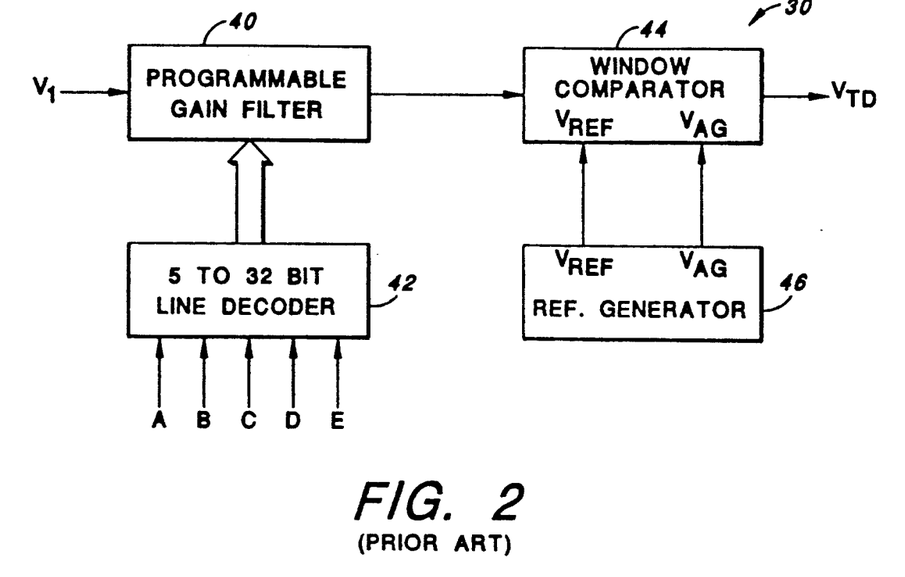
FIG. 2 is a block diagram of a prior art programmable gain sense amplifier heretofore used with the cardiac pacer of FIG. 1.

Referring next to FIG. 2, a block diagram of a prior art sense amplifier 30 is shown. The electrogram signal $V_1$ from the electrogram lead is coupled to a programmable gain filter 40, which is coupled to a gain decoder 42 and a window comparator 44. The window comparator is coupled to a constant reference voltage generator (or analog ground voltage generator) 46 and generates the threshold detect (or trigger) signal $V_{TD}$. In operation, the electrogram signal is received by the programmable gain filter 40, which filters undesirable electrogram signal components (noise), from the desirable electrogram signal components. The programmable gain filter 40 also amplifies the electrogram signal in accordance with a programmable amplitude gain. The programmable amplitude gain (or "programmable gain") is "programmed" by a gain signal received from the decoder 42. The gain signal can be adjusted by the pacing controller 22 (FIG. 1), which provides a gain code to the decoder 42. The decoder 42 generates the gain signal in response to the gain code and thereby "programs" the programmable gain filter 40 to amplify the electrogram signal in accordance with the desired programmable gain.

Typically, the "programming" or varying of the programmable gain in the programmable gain filter 40 is achieved by electronically "substituting," i.e., switching in and out, different sized capacitors into a low pass or high pass stage of the programmable gain filter 40. As such different sized capacitors are substituted or switched in and out of the programmable gain filter 40, the gain of the programmable gain filter 40 changes, i.e., increases or decreases, as is known in the art.

Problematically, as discussed previously, when small capacitors are used within a switched-capacitor programmable gain filter, the inherent parasitic capacitors that are always present within an integrated circuit prevent precise gain changes or gain steps from being realized. As a result, when a desired change (or step) in gain is small, and therefore the difference in size of the capacitors to be substituted for one another is small, the probability exists (due largely to the existence of the parasitic capacitance, which capacitance is not only hard to predict, but typically varies as a function of the switched circuit configuration that is employed at a given time) that the total capacitance (including the parasitic capacitance) of the newly switched capacitor may actually be smaller, instead of larger, than the total capacitance (also including parasitic capacitance) of the previously switched capacitor for which it is substituted, or vice versa. Hence, as the gain code is, e.g., increased, the resultant programmable gain of the amplifier may disadvantageously decrease for any given gain step. Such undesirable operation is known as polytonic operation and, at best, complicates the error correcting functions that must be performed by, e.g., the pacing controller in order to accurately adjust the gain of the programmable gain filter 40.

After being filtered and amplified, the electrogram signal is received by the window comparator 44, which compares the electrogram signal's voltage with a fixed window (or threshold) voltage. As shown in FIG. 2, the window voltage is generated by the analog ground voltage generator 46 wherein the window voltage comprises the potential difference between a reference voltage $V_{REF}$ and an analog ground voltage $V_{AG}$. The analog ground voltage $V_{AG}$ represents the approximate base line, or d.c. voltage offset, of the electrogram signal, and the reference voltage $V_{REF}$ represents some voltage potential or excursion that is higher or lower than the analog ground voltage $V_{AG}$.

In the event that the electrogram signal exceeds the window or threshold voltage, the window comparator generates a threshold detect (or trigger) signal $V_{TD}$, which is coupled to the pacing controller 22 (FIG. 1). Thus, if the programmable gain of the programmable gain filter 40 is selected such that the electrogram signal, after amplification, exceeds the window voltage only when, e.g., the QRS complex appears on the electrogram signal, the pacing controller will receive the threshold detect signal $V_{TD}$ only when the QRS complex appears on the electrogram signal. Thus, the pacing controller 22 (FIG. 1) can adjust the therapy to be delivered to the heart 10 (FIG. 1) in accordance with whether, e.g., the QRS complex is present within the electrogram signal.

Thus, referring again momentarily to FIG. 7, it is seen that the prior art sense amplifier 30 adjusts its sensitivity or sensitivity level by adjusting the gain by which the electrogram signal is amplified, which adjusted gain determines the relationship between the amplified electrogram signal and the fixed reference voltage $V_{WIN}$. For the reasons explained above, the prior art sense amplifier 30, shown in FIG. 2 suffers from inaccuracies, occupies excessive chip area, and can exhibit polytonic sensitivity levels.

Figure 3:
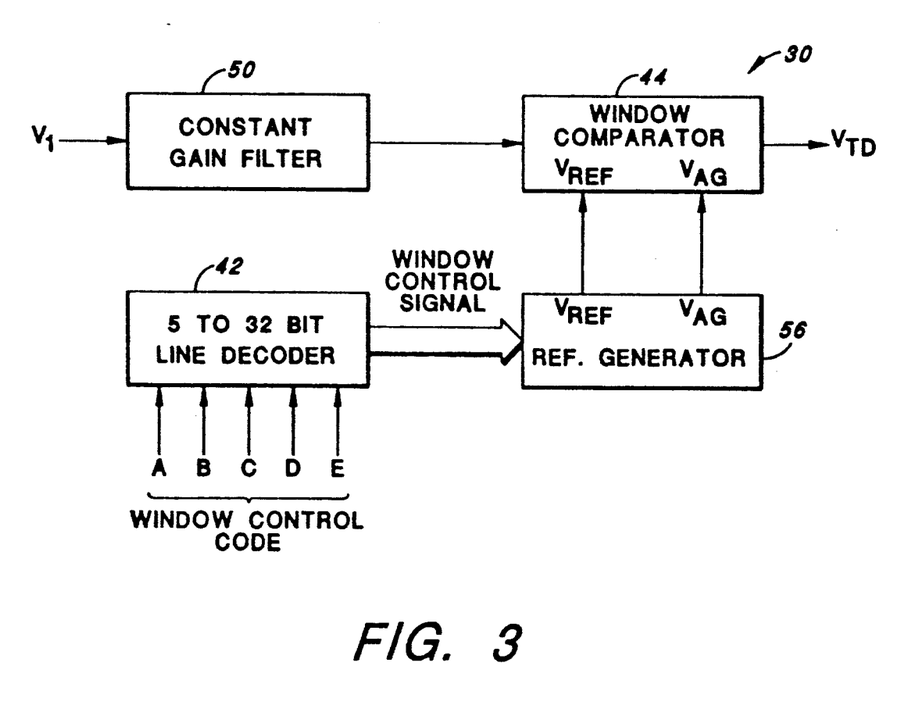
FIG. 3 is a block diagram of a variable reference threshold sense amplifier made in accordance with the present invention.

Referring next to FIG. 3, a block diagram of a sense amplifier 30 made in accordance with the present invention is shown. As seen in FIG. 3, the electrogram signal $V_I$ is coupled to a constant gain filter 50 that is coupled to the window comparator 44. As described above, the window comparator 44 generates a threshold detect signal $V_{TD}$ in response to the electrogram signal when the electrogram signal exceeds the window voltage. The window comparator 44 is also coupled to a variable (or programmable) reference generator 56 that generates a variable reference voltage $V_{REF}$ and the analog ground voltage $V_{AG}$ in response to a window control signal, generated by the decoder 42. The decoder 42, generates the window control signal in response to a window control code received from the pacing controller 22 (FIG. 1).

In operation, the electrogram signal is filtered and amplified by the constant gain filter 50, as described above except that the gain of the constant gain filter 50 is a constant gain, not a programmable gain as in FIG. 2. The filtered and amplified electrogram signal is then coupled to the window comparator 44. In the event that the electrogram signal exceeds the window voltage, the threshold detect signal $V_{TD}$ is generated. However, unlike the programmable gain sense amplifier 30 of FIG. 2, the variable reference threshold sense amplifier 30 of FIG. 3 provides a variable (programmable) window voltage. Specifically, while the analog ground voltage $V_{AG}$ is a fixed voltage, as in FIG. 2, the reference voltage $V_{REF}$ is variable in response to the window control signal.

In accordance with a preferred embodiment of the present invention, the variable reference generator 56 uses a variable emitter area bipolar junction semiconductor device in order to generate the variable reference voltage, $V_{REF}$. Advantageously, because semiconductor devices are realizable with precision in integrated circuit technology, such approach allows the reference voltage, $V_{REF}$, to be more accurately generated, thereby allowing the presence of specified components, e.g., the QRS complex, in the electrogram signal to be detected with more accuracy. Furthermore, the programmable reference generator 56 of the present invention advantageously provides a monotonic variable reference voltage. That is, the reference voltage generated in response to an increasing window control code is always increasing.

The monotonic character described above is achievable primarily because of the manufacturing tolerances involved in the fabrication of semiconductor devices in integrated circuit technology are superior to the manufacturing tolerance associated with small (0.1–0.5 pf) on-chip capacitors; and secondarily because the variable emitter area is always increased by increasing window control codes, as opposed to a substitution of one capacitor for another, as was done in the programmable gain filter of the prior art.

Figure 4:
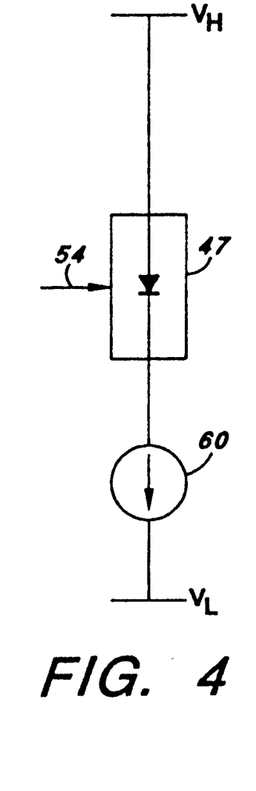
FIG. 4 is a block diagram of a variable emitter area bipolar junction semiconductor device placed in series combination with a constant current source so as to provide a window voltage generator circuit that may be used in the variable reference threshold sense amplifier of FIG. 3.

Referring next to FIG. 4, a block diagram of a variable (or programmable) emitter area bipolar junction semiconductor device 47 is shown. The programmable emitter area bipolar junction semiconductor device 47 is shown in series combination with a constant current source 60 that forces a constant current to flow from a first voltage potential $V_H$ to a second voltage potential $V_L$ through an electrical current path that includes the programmable emitter area bipolar junction semiconductor device 47. The semiconductor device 47 has an emitter area that can be varied or programmed via one or more emitter area control lines 54. In response to one or more control signals received via the control lines 54, the emitter area of the semiconductor device 47 can be made larger or smaller. As a result, the voltage drop across the bipolar junction of the semiconductor device 47 varies in accordance with the following voltage function:

$$V_{REF}(A) = V_T \ln\left(\frac{I}{AJ_s}\right) \quad (1)$$

where V(A) is the voltage drop across the bipolar junction of the semiconductor device 47, $V_T$ is a thermal voltage, I is the constant current through the device, A is the emitter area of the device, and $J_S$ is the current density in the device. Thus, as the emitter area A is increased, the voltage drop V(A) across the semiconductor device, decreases; and as the emitter area A is decreased, the voltage drop V(A) increases.

Figure 5:
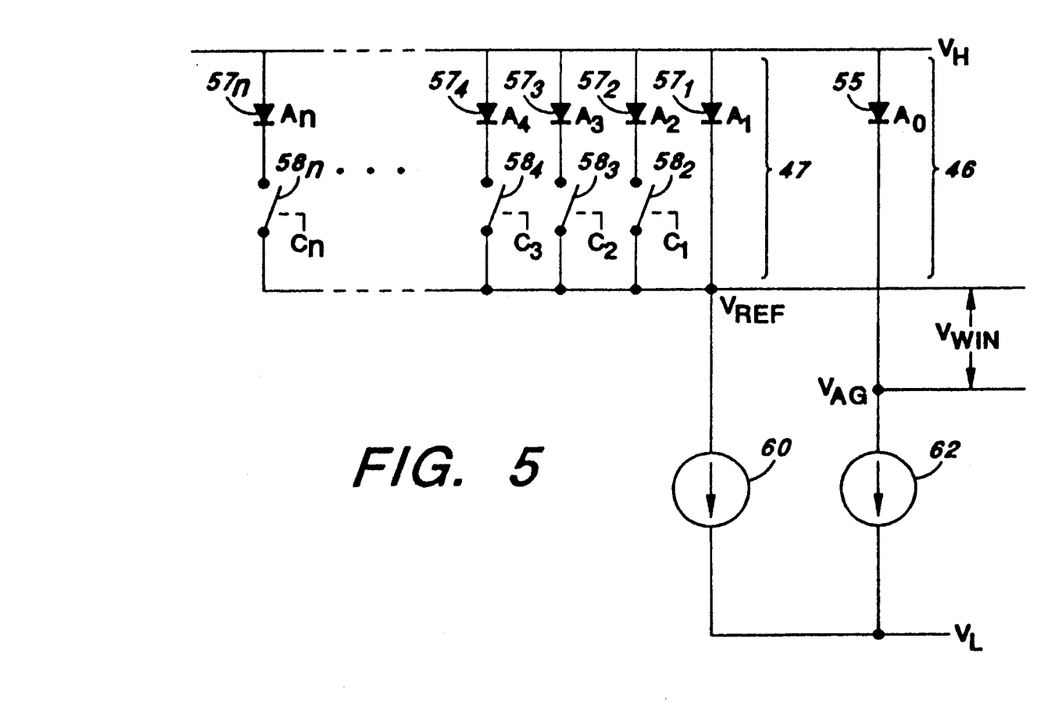
FIG. 5 is a schematic diagram showing one embodiment of the variable emitter area bipolar junction semiconductor device of FIG. 4 that utilizes switched bipolar junction semiconductor devices.

A particular technique that may be used to realize the variable emitter area bipolar junction semiconductor device 47 of FIG. 4 is shown in FIG. 5. Such technique uses switched bipolar junction semiconductor devices 57 to vary the total emitter area of the semiconductor device 47. Switched bipolar junction semiconductor devices $57_2$, $57_3$, ... $57_n$ are in a parallel combination with each other and with one non-switched semiconductor device $57_1$. Any number n of semiconductor devices may be used. Such parallel combination forms the variable emitter area semiconductor 47, which semiconductor 47 is in series with the constant current source 60. Each of the switched semiconductor devices $57_2$, $57_3$, $57_4$ ... $57_n$ is in series with a respective switching element $58_2$, $58_3$, $58_4$ ... $58_n$ that can be in a closed position or an open position as a function of respective control signals $C_2$, $C_3$, ... $C_n$. When a given switching element, e.g., $58_2$, is in a closed position, a portion of the constant current flows though the switched semiconductor device, e.g., $57_2$, in series therewith. The switching elements $58_2$, $58_3$, $58_4$ ... $58_n$ are controlled to be in the open or closed position by one or more control signals $C_2$, $C_3$, ... $C_n$. Thus, each of the switched semiconductor devices $57_2$, $57_3$, $57_4$ ... $57_n$ will either have or not have a portion of the constant current flowing through it in accordance with whether each of the corresponding switching elements $58_2$, $58_3$, ... $58_n$ is open or closed. As more of the switching elements are closed, more emitter area is added to the semiconductor device, and as a result the reference voltage $V_{REF}$, measured at a reference point interposed between the semiconductor device 47 and the constant current source 60, becomes smaller.

Included in the configuration shown in FIG. 5 is an analog ground voltage generator 46 comprising a fixed emitter area bipolar junction device 67 in series with another constant current source 62 connected between the first voltage $V_H$ and the second voltage $V_L$. The fixed emitter area bipolar junction device 55 has a fixed emitter area $A_0$ and the voltage drop across the fixed emitter area bipolar junction device 55 is determined according to the following relationship:

$$V_{AG} = V_T \ln\left(\frac{I}{A_0 J_s}\right) \quad (2)$$

where $V_{AG}$ is the voltage drop across the bipolar junction of the fixed emitter area bipolar junction device 55, $V_T$ is the thermal voltage $$\left(=\frac{kT}{q}\right),$$

I is the constant current through the device, $A_0$ is the emitter area of the device, and $J_S$ is a current density in the device. The analog ground voltage, $V_{AG}$, is measured at a point interposed between the fixed emitter area bipolar junction device 55 and the constant current source 62. The current I that flows as a result of the constant current source 62 may be the same as the current I that flows as a result of the constant current source 60.

The threshold or window voltage $V_{WIN}(A)$ used by the present invention is defined as the voltage difference between the reference voltage $V_{REF}$ and the analog ground voltage $V_{AG}$. Thus, the window voltage $V_{WIN}(A)$ can be expressed as:

$$V_{WIN}(A) = V_{AG} - V_{REF}(A) = V_T \ln\left(\frac{I}{A_0 J_s}\right) - V_T \ln\left(\frac{I}{AJ_s}\right) \quad (3)$$

where $V_{WIN}(A)$ is the voltage across the bipolar junction of the variable emitter area semiconductor device 47, $V_{AG}$ is the voltage drop across the bipolar junction of the fixed emitter area bipolar junction device 55, $V_T$ is the thermal voltage $$\left(=\frac{kT}{q}\right),$$

I is the constant current through the devices (which is assumed to be the same for both current sources 60 and 62), A is the emitter area of the variable emitter area semiconductor device 47, $A_0$ is the emitter area of the fixed emitter area bipolar junction device 55 and $J_S$ is a current density in the devices. Hence, it is seen that the window voltage is a function $V_{WIN}(A)$ of the ratio of emitter areas:

$$V_{WIN}(A) = V_T \ln\left(\frac{A}{A_o}\right) \quad (4)$$

Advantageously, as seen in Eq. (4), while the window voltage is a function of the thermal voltage $V_T$ (which thermal voltage is fairly constant due to the constant body temperature of the patient within whom the pacemaker is implanted), it is not a function of the constant current I or the current density $J_S$. Thus, $V_{WIN}(A)$ is primarily only a function of the ratio of A to $A_0$. Moreover, Eq. (4) clearly shows that the window voltage increases as the emitter area of the variable emitter area semiconductor device increases.

Thus, through use of the circuit of FIGS. 4 and 5, a precise window voltage may be generated in response to one or more control signals using a device that can be fabricated using conventional integrated circuit technology.

Figure 6:
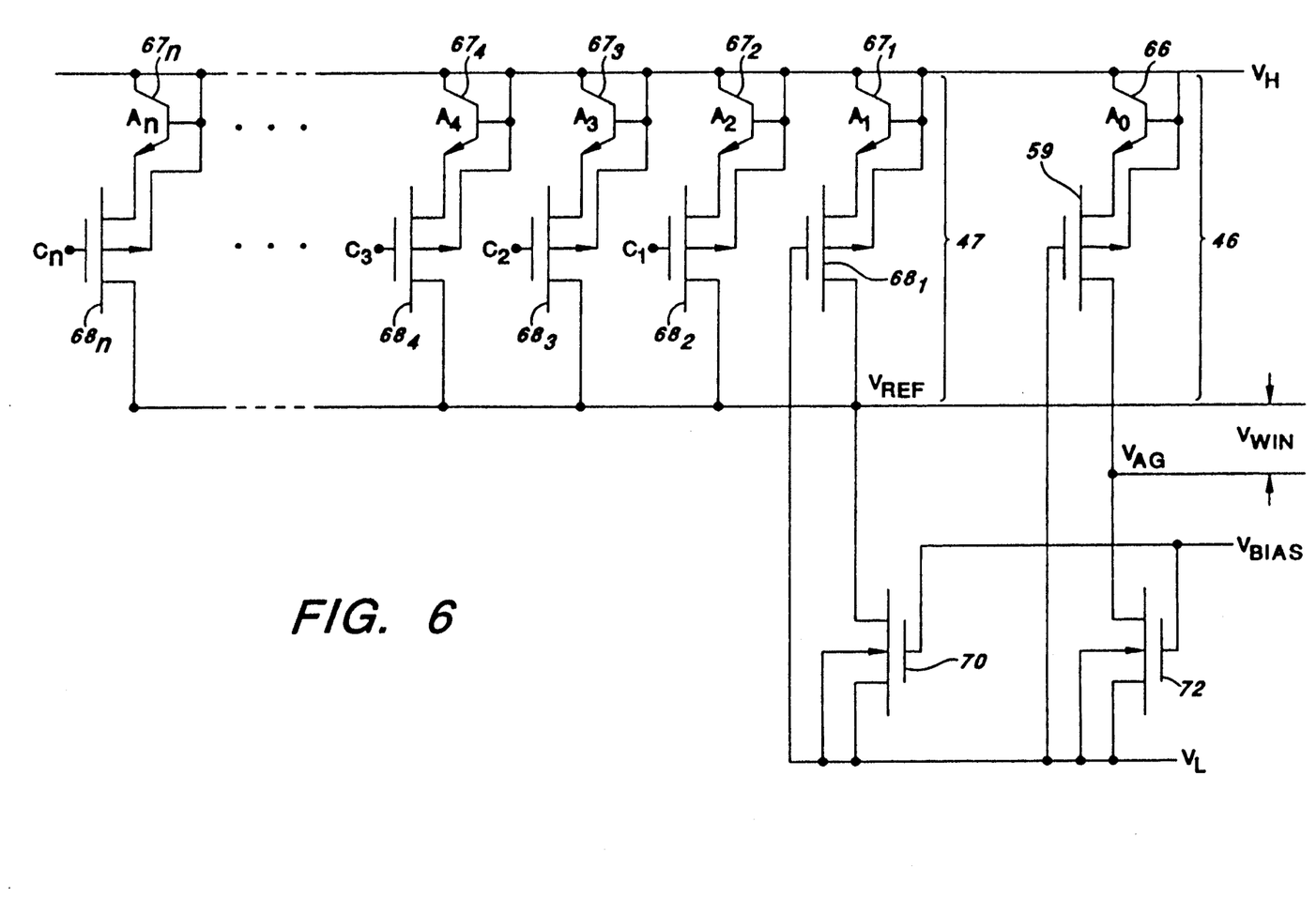
FIG. 6 is a schematic diagram of one embodiment of FIG. 5 wherein the switched bipolar junction devices are realized using bipolar junction transistors in series with field effect transistors.

Referring next to FIG. 6, a schematic diagram showing a particular implementation of FIG. 5 is shown wherein the bipolar junction devices 57 are realized using diode connected bipolar junction devices 67 in series with P-type field effect transistors 68. That is, as seen by comparing FIG. 5 with FIG. 6, the switching elements 58 (FIG. 5) are realized using metal oxide semiconductor (MOS) P-type field effect transistors (PFET's) 68 (FIG. 6), and the bipolar junction semiconductor devices 57 (FIG. 5) are realized using diode connected bipolar junction transistors 67 (FIG. 6).

Several important aspects of the invention should be noted in conjunction with FIG. 6. First, as seen in FIG. 6, the constant current sources 60, 62 are implemented using biased MOS N-type field effect transistors (NFET's) 70, 72 having appropriately biased gates, as is known in the art. Alternatively, many other suitable constant current sources may be used with the present invention.

Second, as a natural result of fabricating complementary metal oxide semiconductor (CMOS) devices on a semiconductor substrate, "parasitic" bipolar junction transistors are formed in the semiconductor substrate. Such parasitic devices are recognized in the art and usually pose a problem for a circuit designer. In this instance, such parasitic devices can be used to form the bipolar junction devices $57_1$, $57_2$, ... $57_n$, and 55 by connecting "the base" of such devices to "the collector" of such devices, i.e., by connecting the devices in a diode configuration (or diode connecting the devices), as is shown in FIG. 6.

Also of note relative to FIG. 6 are that field effect transistors 68, 59 are connected so as to be held in a "closed" position. Such devices thus serve only to compensate, e.g., for improving matching effects, for the controlled switching elements $68_2$, $68_3$, $68_4$, ... $68_n$.

As described above, it is thus seen that the present invention provides an improved programmable reference voltage generator that can be used in a sense amplifier of an implantable medical device, such as a pacemaker, or elsewhere. Advantageously, such reference voltage generator can be readily fabricated using conventional integrated circuit technology, and provides precise regulation of the reference voltage as a function of a control signal(s).

While the invention described herein has been described with reference to a particular embodiment and application thereof, numerous variations and modifications could be made thereto by those skilled in the art without departing from the spirit and scope of the invention as claimed. Accordingly, the scope of the invention should be determined with reference to the claims set forth below.

What is claimed is:

1. An implantable cardiac pacer for delivering electrical therapy to a heart, said cardiac pacer comprising:

a first connection point through which an input electrogram signal can be received by said cardiac pacer, and a second connection point through which a therapeutic output electrical signal can be delivered by said cardiac pacer;

a pace amplifier coupled to the second connection point so as to deliver the therapeutic output signal to the second connection point;

a pacing controller, coupled to the pace amplifier, that initiates the therapeutic output signal; and a sense amplifier coupled between the pacing controller and the first connection point so as to receive the input electrogram signal from the first connection point, said sense amplifier having a sensitivity that determines when a trigger signal is generated as a function of whether a particular waveform present in the input electrogram signal, said trigger signal being provided to the pacing controller, said sense amplifier including:

a filter circuit coupled to the first connection point, said filter circuit amplifying the input electrogram signal in accordance with a prescribed gain to produce an amplifier electrogram signal;

a window comparator circuit coupled between the filter circuit and the pacing controller that receives the amplified electrogram signal, compares it with a reference voltage, and generates the trigger signal whenever the amplitude of the amplified electrogram signal exceeds the reference voltage; and a programmable threshold reference generator circuit coupled to the window comparator circuit, said programmable threshold reference generator circuit including circuitry for generating said reference voltage as a function of a programmed control signal;

whereby the sensitivity of said sense amplifier may be programmably adjusted by said programmed control signal.

2. The implantable cardiac pacer of claim 1, wherein said programmable threshold reference generator comprises:

a first electrical current path that connects a first voltage potential to a second voltage potential;

a first constant current source interposed in said first electrical current path that forces a first substantially constant current to flow through said current path;

a programmable emitter area bipolar junction device, said bipolar junction device being in series with the first constant current source between the first and second voltage potentials such that at least a first portion of the first constant current flows through the programmable emitter area bipolar junction device; and said programmable emitter area bipolar junction device including an emitter area changing means for changing an emitter area thereof in response to the programmed control signal, a change in the emitter area causing an emitter voltage across the programmable emitter area bipolar junction to also change, said emitter providing a voltage signal from which said reference voltage is derived.

3. The implantable cardiac pacer of claim 2, wherein said emitter changing means comprises:
a first bipolar junction device having a first prescribed emitter area, said first bipolar junction device being in series with the first constant current source between the first and second voltage potentials such that at least said first portion of the first constant current flows through the first bipolar junction device; and
a first switched bipolar junction element in a parallel combination with said first bipolar junction device, said first switched bipolar junction element including a second bipolar junction device in series with a respective switching means, said second bipolar junction device having a second prescribed emitter area, and the respective switching means being capable of assuming a closed state and an open state;
said first switched bipolar junction element also being in series with the first constant current source such that at least a second portion of the first constant current flows through the second bipolar junction device when its respective switching means is in its closed state.

4. The implantable cardiac pacer of claim 3, wherein at least said first and second portions of said first constant current flow through said first bipolar junction device when the respective switching means of said second bipolar junction device is open.

5. The implantable cardiac pacer of claim 3, wherein said first and second bipolar junction devices comprise diode-connected parasitic bipolar junction transistors; and
said respective switching element of said second bipolar junction device comprises a field effect transistor.

6. The implantable cardiac pacer of claim 3, further including an analog ground voltage generator circuit comprising:
a second electrical current path that connects the first voltage potential to the second voltage potential;
a second constant current source interposed in the second electrical current path that forces a second substantially constant current to flow through said second current path; and
a fixed emitter area bipolar junction device having a constant emitter area, said bipolar junction device being in series with the second constant current source such that the second constant current flows through the fixed emitter area bipolar junction device, said constant emitter area causing an analog ground voltage to appear across the constant emitter area bipolar junction device;
said reference voltage being derived from a combination of said analog ground voltage of said second electrical current path and said emitter voltage of said first electrical current path.

7. The implantable cardiac pacer of claim 6, wherein said reference voltage comprises the voltage difference between said reference voltage and said analog ground voltage.

8. The implantable cardiac pacer of claim 6, wherein said first and second constant currents are substantially the same.

9. The implantable cardiac pacer of claim 1, wherein said first and second connection points comprise the same point.

10. A sense amplifier for use in a cardiac pacer for delivering electrical therapy to a heart, said sense amplifier comprising:
a constant gain filter that amplifies an input signal in accordance with a prescribed gain to produce an amplifier input signal;
a window comparator circuit coupled to the constant gain filter that compares the amplified input signal with a window voltage and generates a trigger signal whenever the amplitude of the amplifier input signal exceeds said window voltage;
a programmable threshold reference generator circuit that generates a reference voltage, said reference voltage being used to derive the window voltage, said programmable threshold reference generator including:
a first electrical current path that connects a first voltage potential to a second voltage potential;
a first constant current source interposed in the first electrical current path that forces a substantially constant current to flow through said first current path; and
a programmable emitter area bipolar junction device, said programmable emitter area bipolar junction device being in series with the first constant current source such that at least a first portion of the constant current flows through the programmable emitter area bipolar junction device;
said programmable emitter area bipolar junction device including an emitter area changing means for changing an emitter area thereof in response to a control signal, a change in the emitter area causing an emitter voltage across the programmable emitter area bipolar junction to also change, said emitter voltage providing a voltage signal from which said reference voltage is derived;
whereby the programmable threshold reference generator controls the reference voltage in response to the control signal.

11. The sense amplifier of claim 10, wherein said emitter changing means comprises:
a first bipolar junction device having a first prescribed emitter area, said first bipolar junction device being in series with the first constant current source between the first and second voltage potentials such that at least said first portion of the first constant current flows through the first bipolar junction device; and
a first switched bipolar junction element in a parallel combination with said first bipolar junction device, said first switched bipolar junction element including a second bipolar junction device in series with a switching means, said second bipolar junction device having a second prescribed emitter area, and the switching means being capable of assuming a closed state and an open state;
said first switched bipolar junction element also being in series with the first constant current source such that at least a second portion of the first constant current flows through the second bipolar junction device when the switching means is in the closed state.

12. The sense amplifier of claim 11, further including an analog ground voltage generator circuit comprising:
   a second electrical current path that connects a first voltage potential to the second voltage potential;
   a second constant current source interposed in the second electrical current path that forces a second substantially constant current to flow through said second current path; and
   a fixed emitter area bipolar junction device having a constant emitter area, said bipolar junction device being in series with the second constant current source such that the second constant current flows through the fixed emitter area bipolar junction device, said constant emitter area causing an analog ground voltage to appear across the constant emitter area bipolar junction device;
   said analog ground voltage being combined with said reference voltage to generate said window voltage.

13. The sense amplifier of claim 12, wherein said window voltage comprised the voltage difference between said reference voltage and said analog ground voltage.

14. The sense amplifier of claim 12 wherein said first and second constant currents are substantially the same.

15. A sense amplifier for use in a cardiac pacer for delivering therapy to a heart, said sense amplifier comprising:
   amplifying means for amplifying an input electrical signal in accordance with a prescribed gain and producing an amplified input signal;
   comparing means coupled to the amplifying means for comparing the amplified input signal with a window voltage and for generating a trigger signal whenever the amplified input signal exceeds the window voltage;
   reference generation means coupled to the comparing means for generating a reference voltage, said reference voltage being used to derive the window voltage, said reference generation means including:
      a first electrical current path that connects a first voltage potential to a second voltage potential;
      first current source means interposed in the first electrical current path for forcing a substantially first constant current to flow through said current path; and
      programmable emitter area means for generating a programmable emitter voltage, said programmable emitter area means being in series with the first current source means such that at least a first portion of the first constant current flows through the programmable emitter area means, said programmable emitter area means including an emitter area changing means for changing an emitter area of the programmable emitter area means in response to a control signal, a change in the emitter area causing the emitter voltage across the programmable emitter area means to also change, said emitter voltage providing the reference voltage from which said window voltage is derived.

16. The sense amplifier of claim 15, wherein said emitter changing means comprises:
   a first bipolar junction device having a first prescribed emitter area, said first bipolar junction device being in series with the first current source means such that at least said first portion of the first constant current flows through the first bipolar junction device; and
   a plurality of switched bipolar junction elements in parallel combination with said first bipolar junction device, each of said switched bipolar junction elements including a second bipolar junction device in series with a respective switching means, said second bipolar junction device having a prescribed emitter area, the respective switching means being capable of assuming a closed state or an open state as a function of a control signal;
   each of said switched bipolar junction elements also being in series with the first current source means such that a portion of the first constant current flows through each of said bipolar junction devices when the respective switching means is in the closed state.

17. The sense amplifier of claim 16, further including analog ground voltage generating means for generating an analog ground voltage signal that is combined with said reference voltage to produce said window voltage, said analog ground voltage generating means comprising:
   a second electrical current path that connects the first voltage potential to the second voltage potential;
   second current source means interposed in the second electrical current path that forces a second substantially constant current to flow through said second current path;
   fixed emitter area means for generating an analog ground voltage, said fixed emitter area means having a constant emitter area and being in series with the second current source means such that the second constant current flows through the fixed emitter area means, causing the analog ground voltage to appear across the fixed emitter area means.

18. The sense amplifier of claim 17, wherein said window voltage comprises the voltage difference between said reference voltage and said analog ground voltage.

19. A voltage reference generator circuit for generating a reference voltage, said reference generator including:
   a first electrical current path that connects a first voltage potential to a second voltage potential;
   a first constant current source interposed in said electrical current path that forces a first substantially constant current to flow through said current path; and
   a programmable emitter area bipolar junction device, said programmable emitter area bipolar junction device being in series with the first constant current source between the first and second voltage potentials such that the first constant current flows through the programmable emitter area bipolar junction device;
   said programmable emitter area bipolar junction device including emitter area changing means for changing an emitter area of the programmable emitter area bipolar junction device, a change in the emitter area causing an emitter voltage across the programmable emitter area bipolar junction to also change;
   said emitter voltage providing a stable reference voltage that varies as a function of the emitter area of said programmable emitter area bipolar junction device;
   said reference voltage being derived from said emitter voltage.

20. The voltage reference generator of claim 19, further including an analog ground voltage generator circuit comprising:
- a second electrical current path that connects the first voltage potential to the second voltage potential;
- a second constant current source interposed in the second electrical current path that forces a second substantially constant current to flow through said second current path;
- a fixed emitter area bipolar junction device having a fixed emitter area, said fixed emitter area bipolar junction device being in series with the second constant current source such that the second constant current flows through the fixed emitter area bipolar junction device, causing a second emitter voltage to appear across the fixed area bipolar junction device as a function of its fixed emitter area and the second constant current, said second emitter voltage comprising an analog ground voltage;
- said analog ground voltage being combined with said reference voltage to generate said window voltage.

21. The implantable cardiac pacer or claim 20, wherein said window voltage comprises the voltage difference between said reference voltage and said analog ground voltage.

22. A window reference generator for generating a window voltage including:
- a first electrical current path connected between a first voltage potential and a second voltage potential;
- a first constant current source interposed in said first electrical current path that forces a substantially constant current to flow through said first current path;
- a first bipolar junction device, said first bipolar junction device having a first prescribed emitter area;
- said first bipolar junction device being in series with the first constant current source in the first electrical current path such that at least a portion of the first constant current flows through the first bipolar junction device;
- a switched bipolar junction element in a parallel combination with the first bipolar junction device, said switched bipolar junction element including a plurality of second bipolar junction devices, each being in series with a respective switching means, and each having a prescribed emitter area and being in series with the first constant current source in the first electrical current path, the respective switching means of each of the second bipolar junction devices being capable of assuming a closed state or an open state as a function of a control signal, said closed state allowing at least a portion of said first constant current to flow through whichever of the second bipolar junction devices has its respective switching means in said closed state;
- a reference terminal in series with and interposed between the constant current source and the parallel combination of the first bipolar junction device and the switched bipolar junction element, an adjustable reference voltage appearing between the reference terminal and at least one of the first or second voltage potentials as a function of how many of the respective switching means of the plurality of second bipolar junction devices are in their closed state;
- said reference voltage being used to derive the window voltage;
- whereby said window voltage varies as a function of said control signal.

23. The window reference generator of claim 22, further including an analog ground voltage generator circuit comprising:
- a second electrical current path that connects the first voltage potential to the second voltage potential;
- a second constant current source interposed in the second electrical current path that forces a second substantially constant current to flow through said second current path; and
- a fixed emitter area bipolar junction device, said fixed emitter area bipolar junction device being in series with the second constant current source such that the second constant current flows through the fixed emitter area bipolar junction device;
- said fixed emitter area bipolar junction device having a fixed emitter area, said fixed emitter area causing an analog ground voltage to appear across the fixed emitter area bipolar junction device as said second constant current flows therethrough;
- said window voltage comprising the voltage difference between said reference voltage and said analog ground voltage.

* * * * *